United States Patent [19]

Gal et al.

[11] Patent Number: 5,246,292
[45] Date of Patent: Sep. 21, 1993

[54] TEMPERATURE MEASUREMENT APPARATUS

[76] Inventors: Eli Gal, 8 Albert Lane, Ramat Gan; Dan Moran, 19 Aluf David Street, Ramat Chen; Yonatan Gerlitz, 24 Uri Street, Herzlia, all of Israel

[21] Appl. No.: 890,534

[22] Filed: May 28, 1992

[51] Int. Cl.$^5$ .............. G01K 1/20; G01J 5/08; G01J 5/62; G01J 5/10
[52] U.S. Cl. ............... 374/121; 128/736; 128/664; 374/130; 374/133; 374/129
[58] Field of Search ............ 374/128, 129, 130, 133, 374/121; 128/736, 664; 250/351

[56] References Cited

U.S. PATENT DOCUMENTS

| | | | |
|---|---|---|---|
| 2,920,485 | 1/1960 | Derganc | 374/129 |
| 3,091,693 | 5/1963 | Rudomanski et al. | 374/129 |
| 3,293,915 | 12/1966 | Banca et al. | 374/129 |
| 3,463,006 | 8/1969 | Paddock et al. | 374/29 |
| 3,611,806 | 10/1971 | Hishikari | 374/129 |
| 3,766,781 | 10/1973 | Roberts | 374/128 |
| 3,884,075 | 5/1975 | Brandli et al. | 374/129 |
| 4,005,605 | 2/1977 | Michael | 374/129 |
| 4,031,365 | 6/1977 | Raggiotti et al. | 374/183 |
| 4,045,670 | 8/1977 | Anderson et al. | 374/129 |
| 4,072,863 | 2/1978 | Roundy | 250/332 |
| 4,148,304 | 4/1979 | Mull | 128/736 |
| 4,375,033 | 2/1983 | Bjorkholm et al. | 250/251 |
| 4,396,020 | 8/1983 | Wolff et al. | 128/736 |
| 4,602,642 | 7/1986 | O'Hara et al. | 128/730 |
| 4,611,153 | 9/1986 | Wesling | 318/139 |
| 4,634,294 | 1/1987 | Christol et al. | 374/170 |
| 4,693,615 | 9/1987 | Kyriakis | 374/129 |
| 4,743,122 | 5/1988 | Yamano et al. | 374/128 |
| 4,771,791 | 9/1988 | Kubouchi | 128/736 |
| 4,784,149 | 11/1988 | Berman et al. | 128/736 |
| 4,790,324 | 12/1988 | O'Hara et al. | 128/736 |
| 4,797,840 | 1/1989 | Fraden | 374/133 |
| 4,887,229 | 12/1989 | Weiss | 374/128 |
| 4,907,895 | 3/1990 | Everest | 374/128 |
| 4,932,789 | 6/1990 | Egawa et al. | 374/128 |
| 4,955,727 | 9/1990 | Weiss | 374/128 |
| 4,986,672 | 1/1991 | Beynon | 374/130 |
| 5,001,657 | 3/1991 | Yagura et al. | 374/121 |
| 5,017,018 | 5/1991 | Iuchi et al. | 128/736 |
| 5,018,872 | 5/1991 | Susynski et al. | 374/133 |
| 5,123,751 | 6/1992 | Baker | 374/130 |
| 5,157,684 | 10/1992 | Benda et al. | 372/95 |

FOREIGN PATENT DOCUMENTS

| | | | |
|---|---|---|---|
| 0022060 | 1/1981 | European Pat. Off. | 128/736 |
| 0424102 | 4/1991 | European Pat. Off. | 128/736 |
| 2241310 | 2/1974 | Fed. Rep. of Germany | 374/127 |
| 2045480 | 10/1980 | United Kingdom | 128/736 |
| 0002876 | 5/1987 | World Int. Prop. O. | 128/736 |

Primary Examiner—William A. Cuchlinski, Jr.
Assistant Examiner—Diego F. F. Gutierrez
Attorney, Agent, or Firm—Ladas & Parry

[57] ABSTRACT

Temperature measurement apparatus comprising an IR temperature change detector, a chopper for intermittently exposing the detector to an object whose temperature is to be measured, and means for providing an output indication representing the temperature of the object in response to the output of the detector, wherein the chopper is driven by a quartz timepiece movement.

9 Claims, 8 Drawing Sheets

TEMPERATURE MEASUREMENT APPARATUS

FIELD OF THE INVENTION

The present invention relates to clinical thermometers generally and more particularly to infra-red sensing clinical thermometers.

BACKGROUND OF THE INVENTION

Various types of infra-red sensing clinical thermometers are known. U.S. Pat. No. 2,920,485 describes the use of a pyrometer and a chopper which is operative to intermittently expose a first temperature sensitive detector to radiation to be measured and a second temperature sensitive detector to a known reference temperature source.

U.S. Pat. No. 3,766,781 describes temperature sensing apparatus including a circular chopper, a reference thermistor and a thermal detector, as well as apparatus for converting the output voltage of the thermal detector into pulses.

U.S. Pat. No. 4,797,840 describes an infrared electronic thermometer and method for measuring temperature which employs a pyroelectric sensor and a shutter assembly and calculates the temperature of an object from the sensed change in temperature detected by the sensor upon opening of the shutter and the ambient temperature of the detector.

Additional patents which are relevant to the subject matter of the present invention include U.S. Pat. No. 5,017,018, describing a clinical thermometer which employs a lens and a concave mirror for directing infra-red radiation to the detector; U.S. Pat. No. 5,018,872 which describes a probe assembly for an infrared thermometer for operative engagement with an ear canal; U.S. Pat. No. 4,743,122, which describes infrared ray temperature measuring apparatus and including a distance keeping member; U.S. Pat. No. 4,790,324 which describes a method and apparatus for measuring internal body temperature utilizing infrared emissions; and U.S. Pat. No. 4,602,642, which describes a method and apparatus for measuring internal body temperature utilizing infrared emissions and employs a thermopile.

Most of the above-mentioned techniques use temperature change sensitive detectors which are very sensitive to the chopping frequency. This leads to bulky and complicated chopper means that has to be accurately controlled to maintain a constant chopping frequency in order to achieve constant responsivity from the detection unit. Other techniques bypass the problem by using other types of detectors or one-pulse detection, which reduces the system precision or complicates the technical solution. The present invention seeks to provide a simultaneous solution to the chopping frequency accuracy, volume of the chopping mechanism and complexity of the apparatus.

The teachings of the above-mentioned prior art documents are hereby incorporated by reference.

SUMMARY OF THE INVENTION

The present invention seeks to provide an improved, low cost infra-red sensing clinical thermometer.

There is thus provided in accordance with a preferred embodiment of the present invention, temperature measurement apparatus comprising an IR temperature change detector, a chopper for intermittently exposing the detector to an object whose temperature is to be measured, and means for providing an output indication representing the temperature of the object in response to the output of the detector, wherein the chopper is driven by a quartz timepiece movement.

Additionally in accordance with a preferred embodiment of the present invention there is provided temperature measurement apparatus comprising an IR temperature change detector, a chopper for intermittently exposing the detector to an object whose temperature is to be measured and calculation means for providing an output indication representing the temperature of the object in response to the output of the detector, the calculation means including empirically derived tables stored in memory which relate measured temperature change and detector temperature to object temperature.

Additionally in accordance with a preferred embodiment of the present invention there is provided temperature measurement apparatus comprising an IR temperature change detector, an heat sink for stabilizing the temperature of the detector, a chopper for intermittently exposing the detector to an object whose temperature is to be measured, wherein the chopper is operative to alternatively reflect to the detector radiation from the detector and direct to the detector radiation received from the object, and calculation means for providing an output indication representing the temperature of the object in response to the output of the detector.

Additionally in accordance with a preferred embodiment of the present invention, there is provided an accurate frequency optical chopper for chopping electromagnetic radiation wherein a time piece quartz movement is used to move the chopper blade, a microprocessor is used to drive the said quartz time piece movement and a crystal circuitry is used to synchronize the movement.

Further in accordance with a preferred embodiment of the present invention there is provided temperature measurement apparatus comprising an IR temperature change detector, a chopper for intermittently exposing the detector to an object whose temperature is to be measured, a memory storing a multiplicity of temperatures taken over a period of time, and means for analyzing said multiplicity of temperatures and for indicating, as a result of the analysis, menstrual status.

BRIEF DESCRIPTION OF THE DRAWINGS

The present invention will be understood and appreciated more fully from the following detailed description, taken in conjunction with the drawings in which:

FIG. 8A illustrates an ovulatory cycle.

DETAILED DESCRIPTION OF THE PRESENT INVENTION

Figure 1:
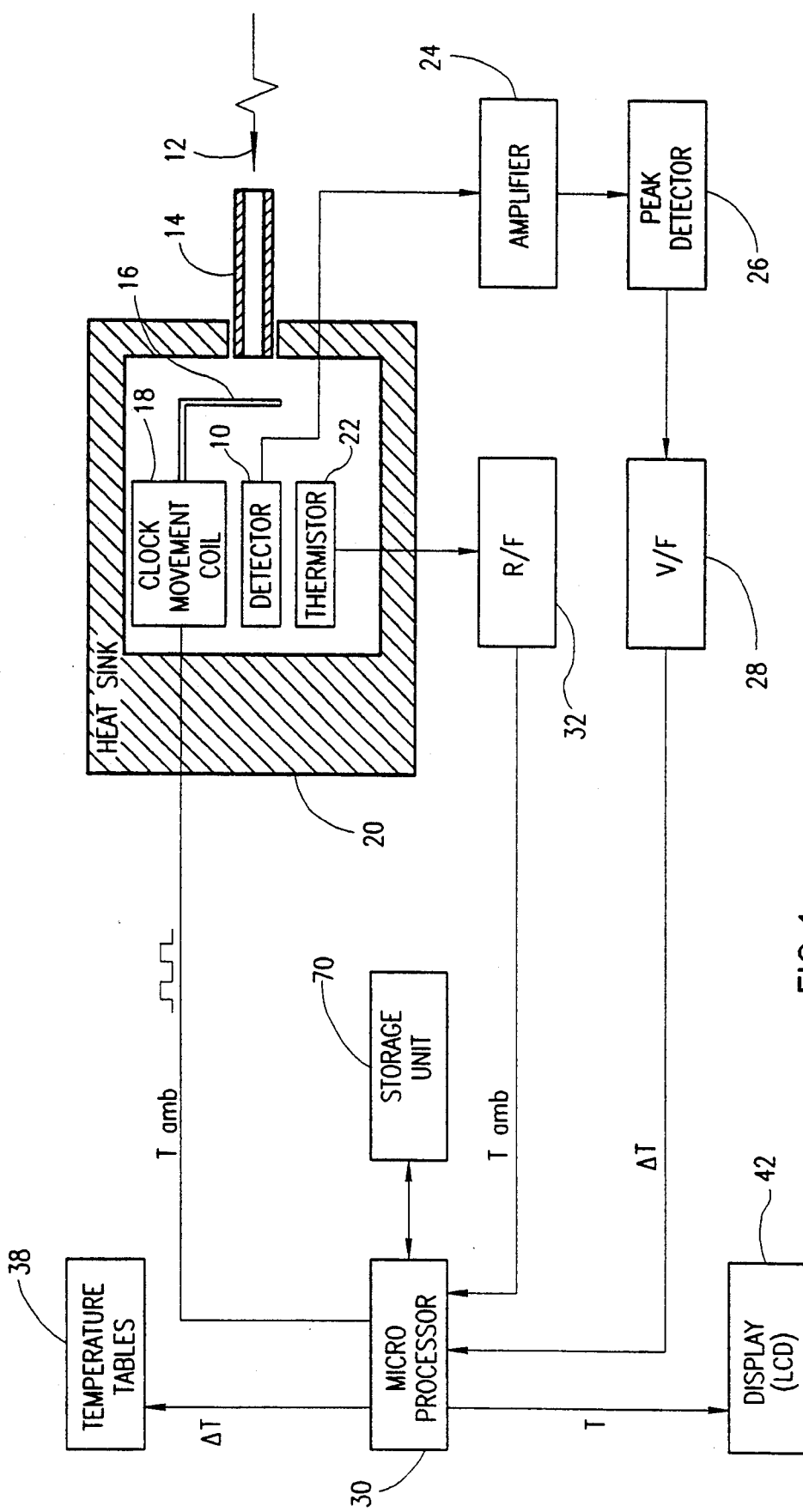
FIG. 1 is a block diagram illustration of a clinical thermometer constructed and operative in accordance with a preferred embodiment of the present invention.

Reference is now made to FIGS. 1, 2A, 2B and 5, which illustrate an IR clinical thermometer constructed and operative in accordance with a preferred embodiment of the present invention. The thermometer comprises an IR detector, such as a pyro-electric detector 10, such as a P2288-10 of Hamamatsu, which receives radiation, indicated at reference numeral 12, from an object (not shown) whose temperature is to be measured via a radiation guide tube 14.

A chopper 16 intermittently interrupts the passage of IR radiation 12 to the detector 10. Chopper 16 is required because conventional pyroelectric detectors 10 only measure a change in temperature, rather than an absolute temperature.

In accordance with a preferred embodiment of the present invention, the chopper 16 is driven in reciprocating motion by a crystal controlled timepiece movement 18, such as that commonly employed in watches. Such a movement is characterized in that it uses a very small amount of electrical power (which allows it to be driven directly by the microprocessor), its volume is very small and the chopping frequency achieved from this device is both stable and precise.

When the chopper 16 lies between the detector 10 and the radiation guide tube 14, the detector 10 sees radiation which is reflected by that surface of the chopper 16 which faces the detector 10, from the detector 10 itself, i.e. senses the detector temperature.

In accordance with a preferred embodiment of the present invention, the detector 10 and the movement 18 are mounted or are in close proximity to a common heat sink 20, whose temperature is monitored by a thermistor 22. In this manner, the temperature measured by the detector 10 when the chopper 16 is interposed between the detector and the object whose temperature is to be measured is known.

The output of the detector 10 is supplied via an amplifier 24 and a peak detector 26 to a voltage-to-frequency converter 28, designed with a comparator such as a LM 393 of National Semiconductor. The output of the voltage-to-frequency converter 28 is supplied to a microprocessor 30.

The output of thermistor 22 is supplied via a resistance-to-frequency converter 32, designed with a comparator such as a LM 393 of National Semiconductor, to microprocessor 30.

Figure 2A:
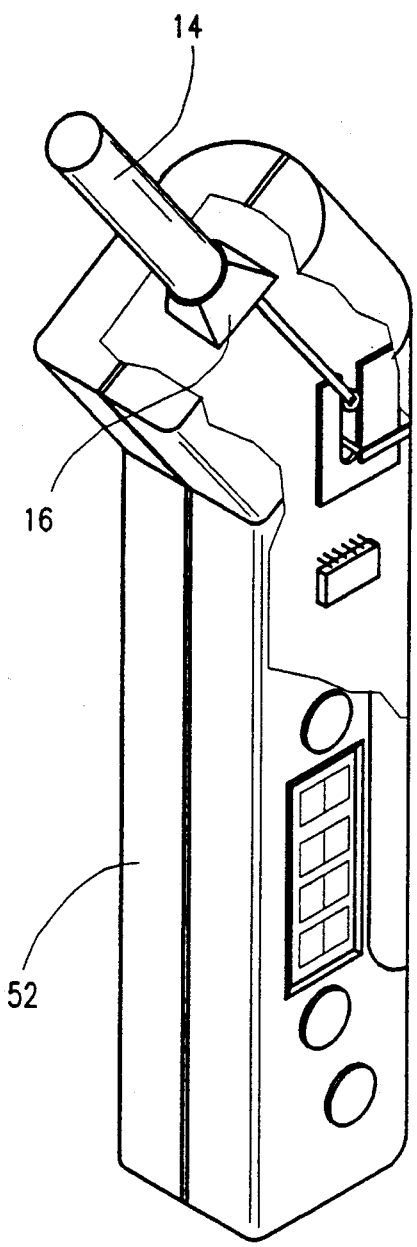
FIGS. 2A and 2B are pictorial illustrations of a clinical thermometer constructed and operative in accordance with a preferred embodiment of the present invention.
Figure 2B:
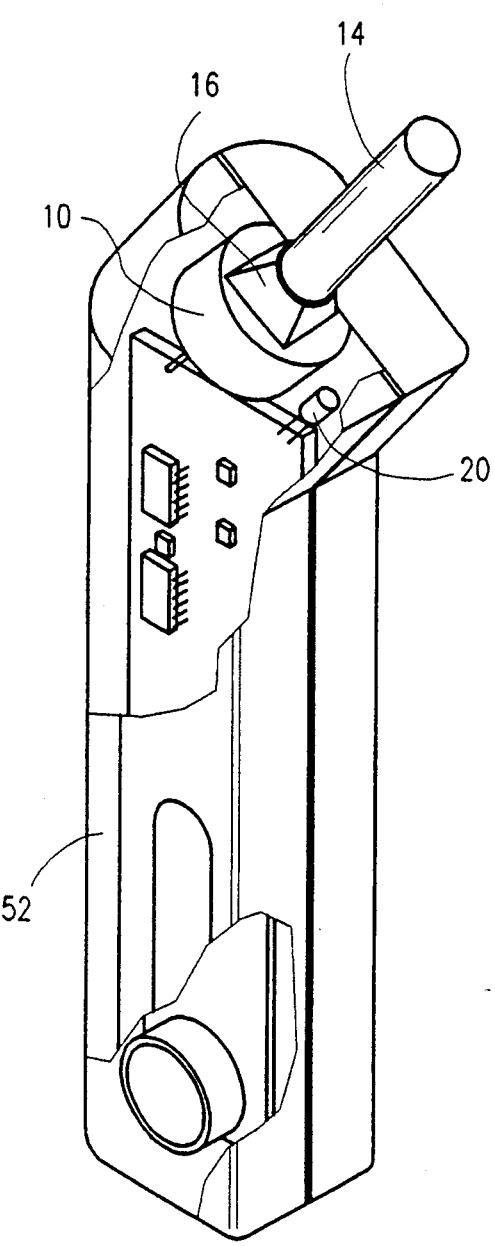
Figure 3B:
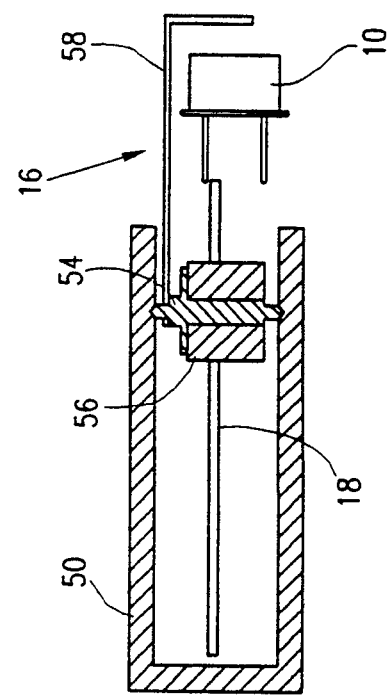
FIGS. 3A and 3B are detailed illustrations of the structure of a chopper mechanism and detector constructed and operative in accordance with a preferred embodiment of the present invention, FIG. 3B being a sectional illustration taken along lines B—B of FIG. 3A.
Figure 3A:
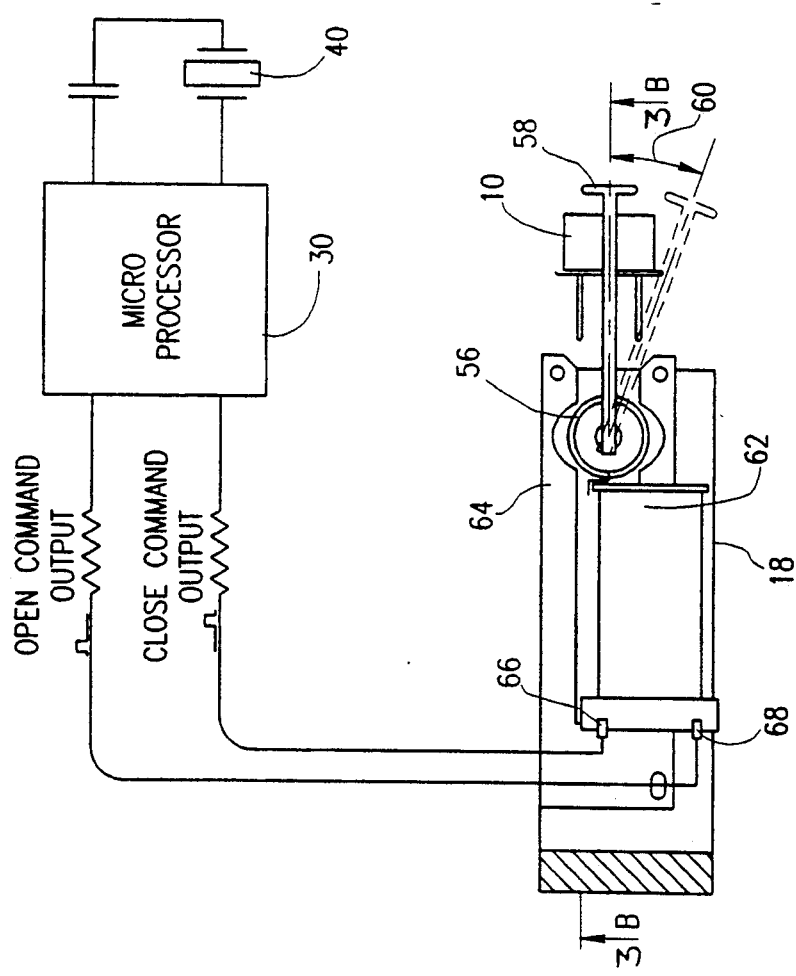
Figure 4:
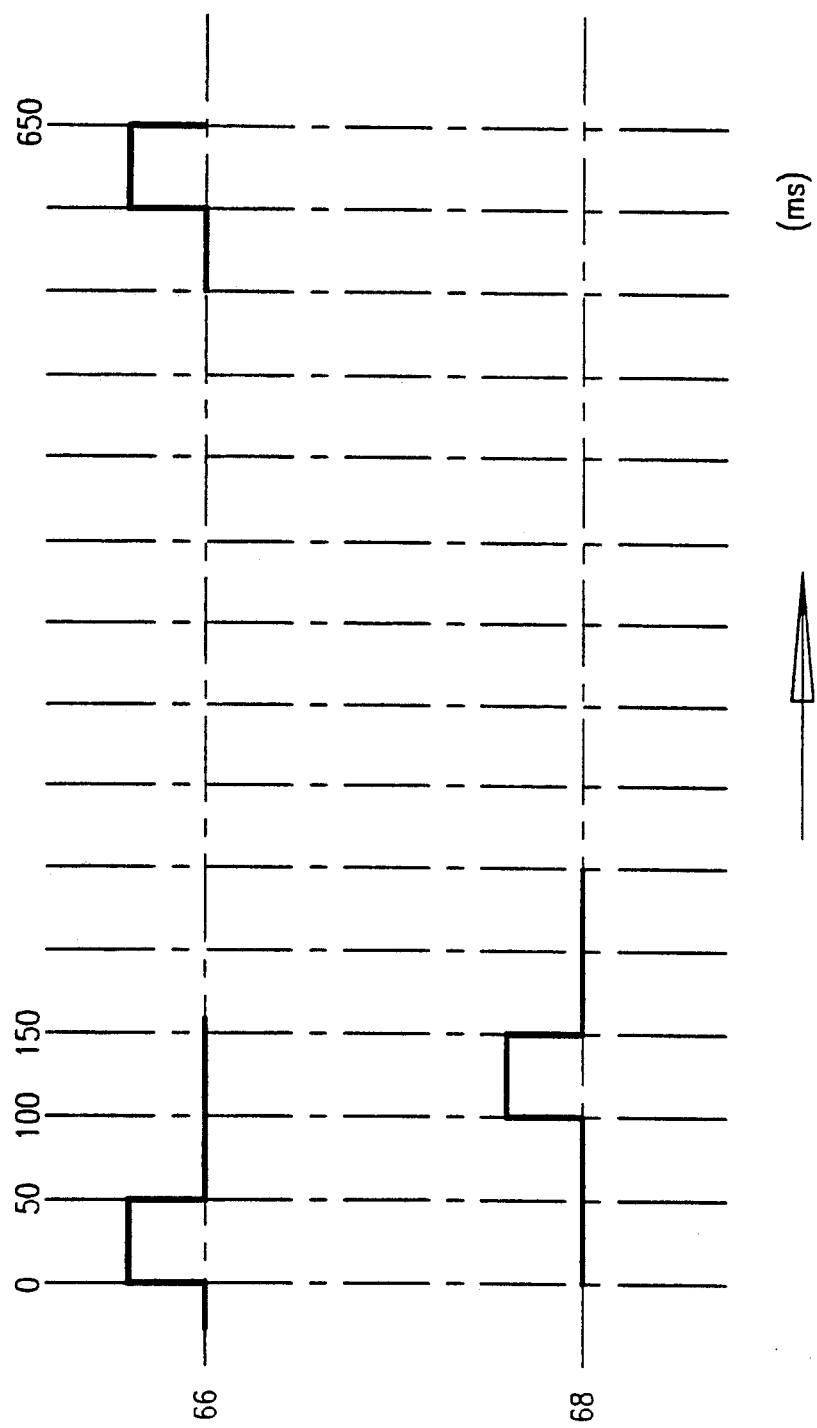
FIG. 4 is a timing diagram illustrating operation of the apparatus of FIG. 3.

The structure of the chopper 16 and movement 18 may be appreciated from a consideration of FIGS. 3A, 3B and 4. As seen in FIGS. 3A and 3B, the movement 18 is enclosed in a housing 50, which may be integrally formed with or alternatively separate from housing 52 of the thermometer (FIGS. 2A and 2B). The movement 18 typically comprises an axle 54 pivotably mounted on housing 50 and a permanent magnet 56 mounted on axle 54. A chopper blade 58, forming the chopper 16, is fixed to axle 54 for reciprocating pivotal movement therewith as illustrated by arrows 60.

The movement 18 further comprises a coil 62 associated with a core 64. The coil 62 receives pulsed inputs at first and second input terminals 66 and 68 from outputs of microprocessor 30 and is operative, in response to the pulsed inputs, to cause magnet 56 and axle 54 to undergo pivotal motion as indicated by arrows 60. Typical timing diagrams of the pulse inputs received at terminals 66 and 68 appear in FIG. 4.

In accordance with a preferred embodiment of the invention, the microprocessor 30 is operative to determine the temperature of the object whose temperature is being measured by employing an ambient temperature input $T_{amb}$ from thermistor 22 via converter 32, which is calibrated by a calibration potentiometer 34 (FIG. 5), and a delta T input from detector 10 via converter 28 which is calibrated by a calibration potentiometer 36.

As opposed to the prior art which calculates the object temperature directly from the inputs to the microprocessor 30, the present invention employs a look up table 38 (FIG. 1) containing various values of delta T and $T_{amb}$ which correspond to the inputs to the microprocessor 30.

Figure 5:
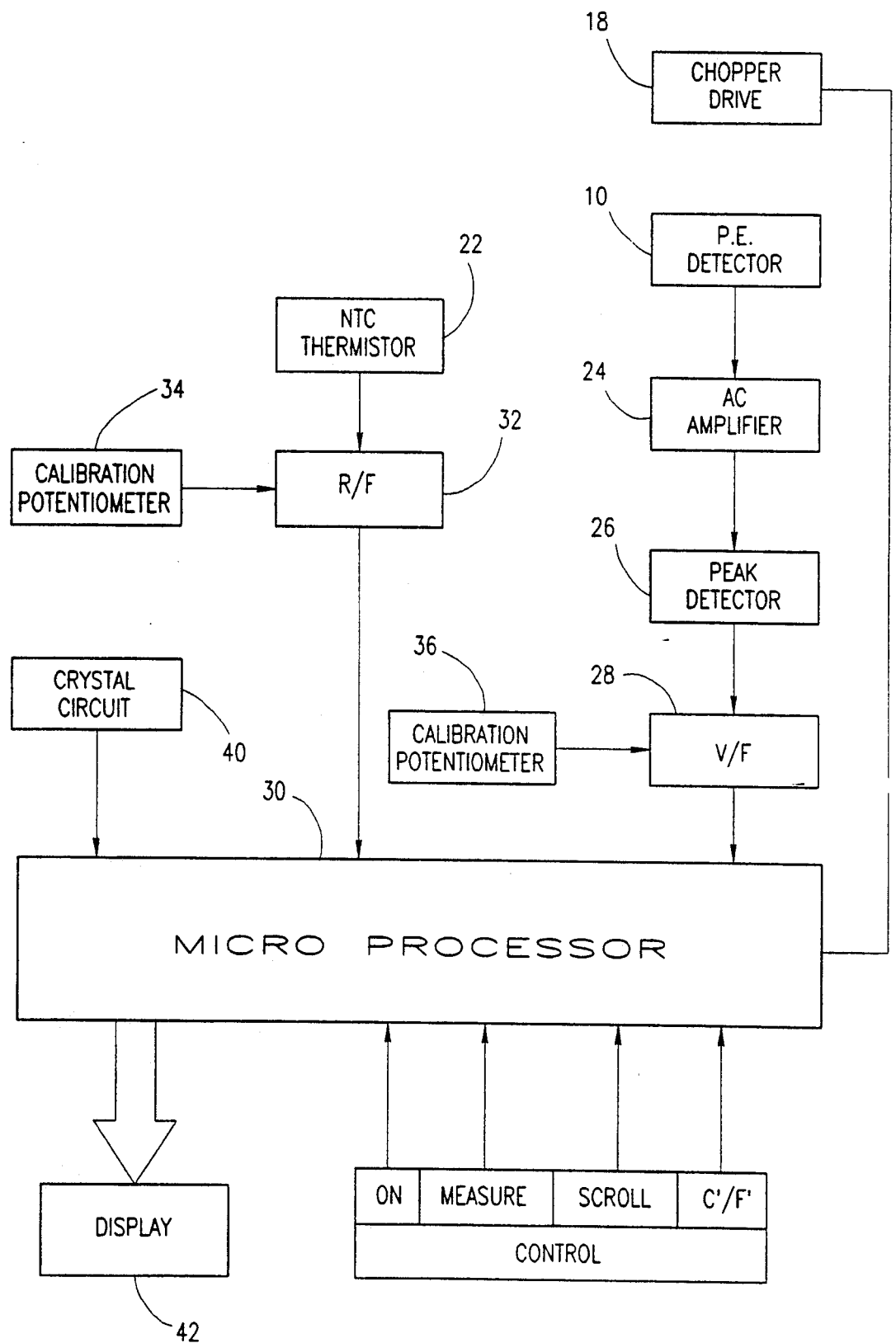
FIG. 5 is an electronic circuit diagram of the apparatus of FIGS. 1-4.
Figure 6:
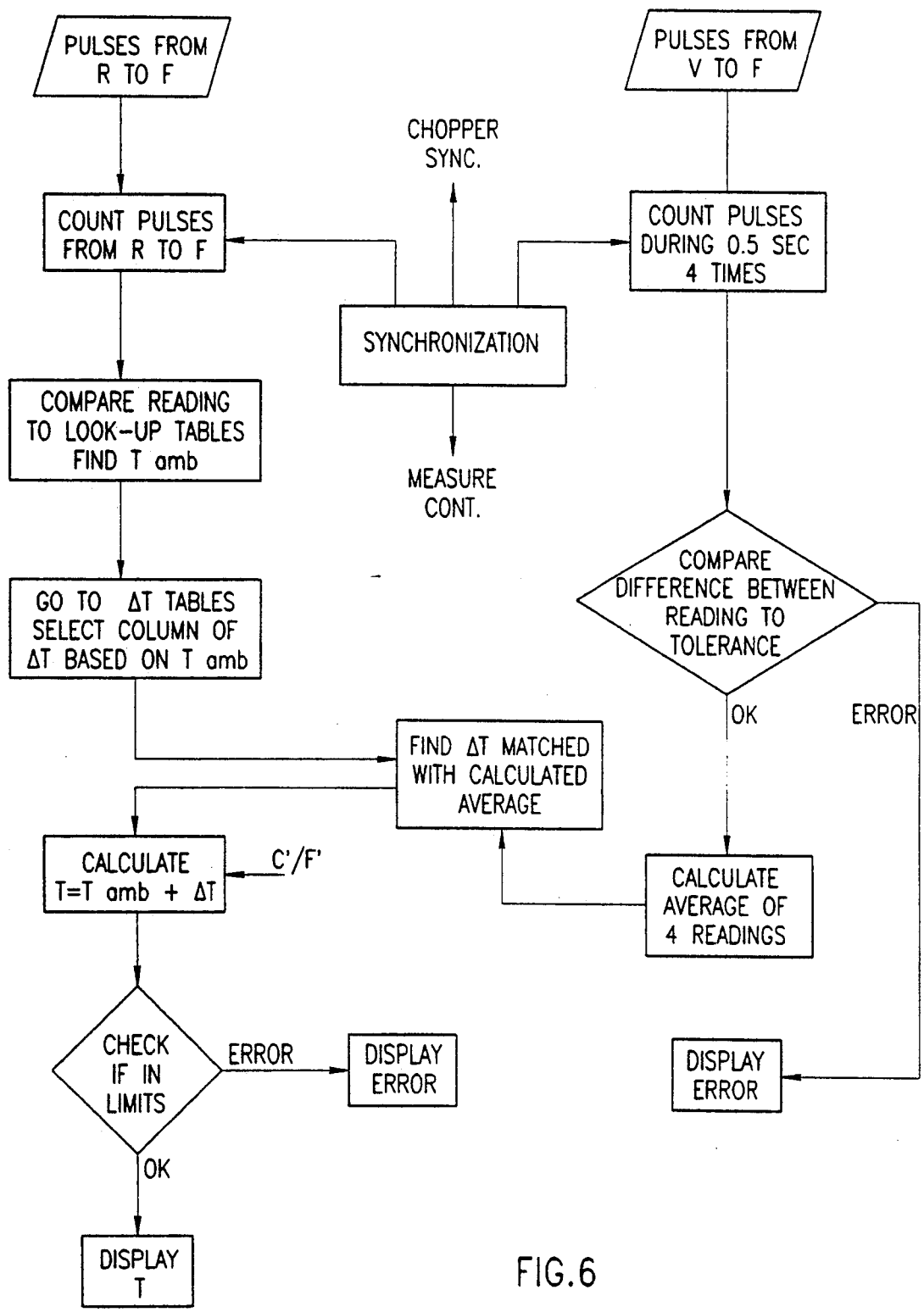
FIG. 6 is a flow chart illustrating the operation of the apparatus of FIG. 5.
Figure 7:
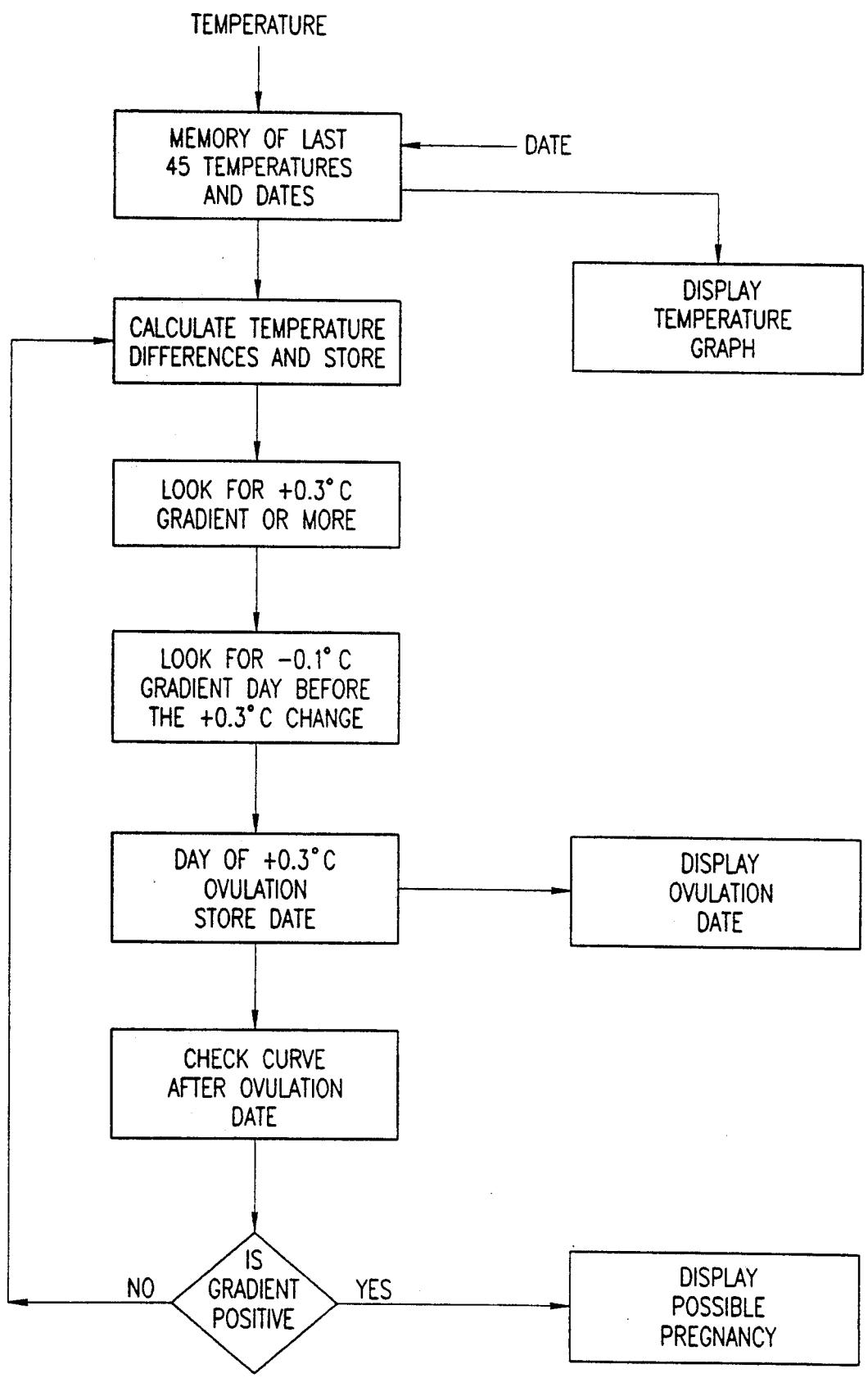
FIG. 7 is a flow chart illustrating the operation of FIG. 5 when performing further computation and analysis of the temperature behavior.

The operation of the microprocessor 30 is summarized in the software diagram of FIG. 6. Pulses from the converter 32, indicating the ambient temperature are counted using the input from a synchronizing clock 40 (FIG. 5). The look up tables 38 are consulted to obtain $T_{amb}$.

The value of delta T is then obtained from look up tables 38 as follows: the pulses received from converter 28 within a predetermined length of time are counted. This operation utilizes the synchronizing clock input from clock 40 and is repeated a plurality of times to produce multiple readings. The differences between the multiple readings are compared to determine if they fit within a predetermined tolerance.

If the multiple readings are not within the predetermined tolerance, an error signal is produced. If the multiple reading are within tolerance, an average of the multiple readings is taken and used to access the look up tables 38 to provide delta T.

The microprocessor 30 then proceeds to calculate the object temperature in a conventional manner. If the temperature result is within applicable limits it is displayed at a display 42 (FIG. 1) otherwise an error signal is displayed.

Reference is now made to FIGS. 7 and 8A, 8B and 8C which illustrate a further embodiment of the present invention for indicating menstrual status, wherein the term "menstral status" is taken to mean whether ovulation or a possible pregnancy have occurred.

Figure 8A:
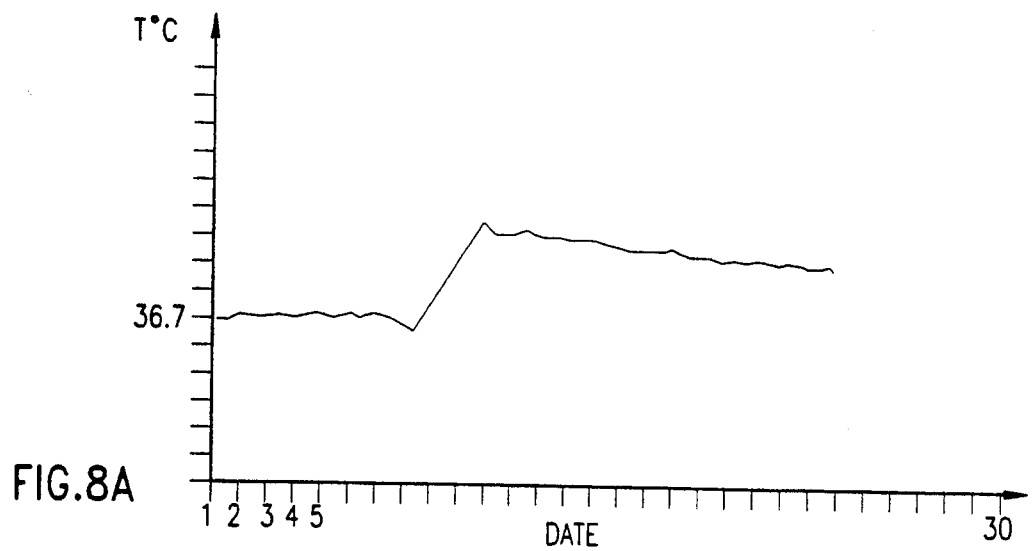
FIGS. 8A, B and C are schematics of typical temperature during the menstral cycle of a woman, where
Figure 8B:
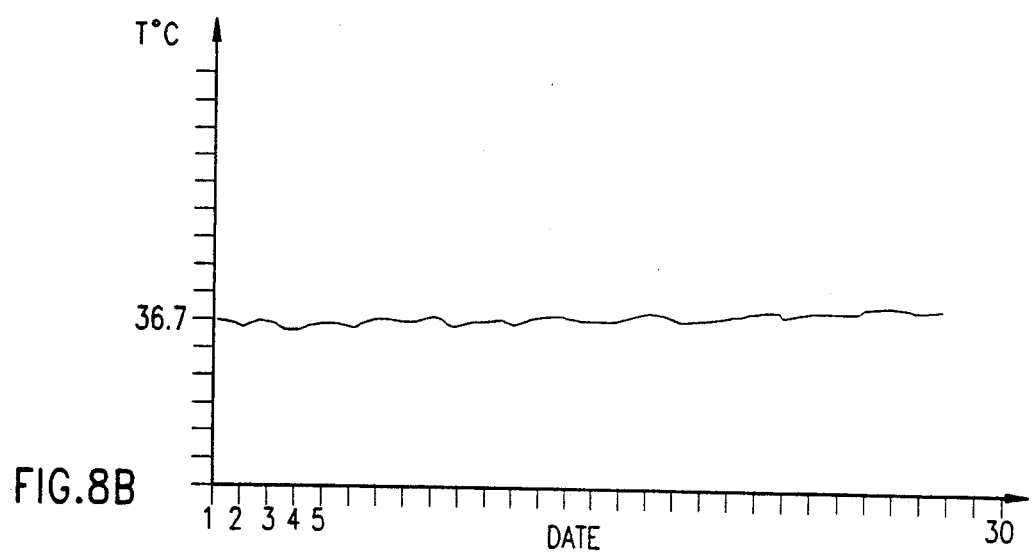
FIG. 8B illustrates an anovulatory cycle and FIG. 8C illustrates a cycle in which conception occurs.
Figure 8C:
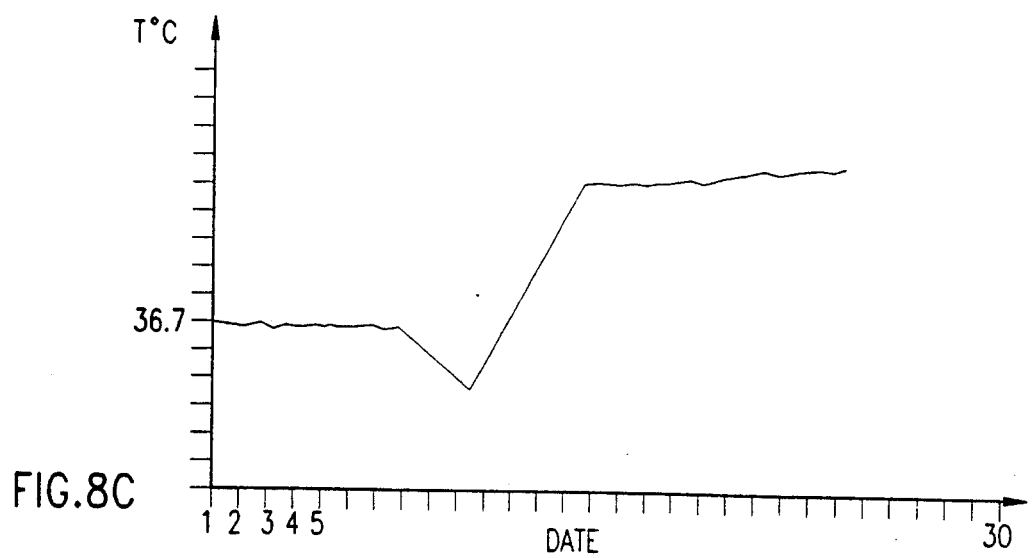

In this embodiment, the clinical thermometer of FIG. 1 additionally comprises a storage unit 70 within which are stored a plurality of temperatures of at least one patient. In this further embodiment, the stored temperatures as well as the currently measured temperature are analysed, in accordance with the method shown in FIG. 7, to indicate whether the temperature behavior is typical of ovulation (FIG. 8A), an anovulatory cycle (FIG. 8B) or possible pregnancy (FIG. 8C). If ovulation or pregnancy is indicated, the appropriate information may be displayed on the display 42.

It will be appreciated by persons skilled in the art that the present invention is not limited by what has been particularly shown and described hereinabove. Rather the scope of the present invention is defined only by the claims which follow:

I claim:

1. Temperature measurement apparatus comprising:
   an IR temperature change detector;
   a chopper for intermittently exposing the detector to an object whose temperature is to be measured; and
   means for providing an output indication representing the temperature of the object in response to an output of the detector,
   wherein said chopper comprises:
   a quartz timepiece movement assembly having a rotating element; and
   a chopper blade mechanically connected to said rotating element for being driven in reciprocating rotational movement thereby.

2. Temperature measurement apparatus according to claim 1 and also comprising:
   empirically derived tables stored in a memory which relate measured temperature change and detector temperature, determined when said chopper prevents radiation from the object to reach the detector, to object temperature.

3. Temperature measurement apparatus according to claim 2 and also comprising means for analyzing and indicating menstrual status by employing said output indication.

4. Temperature measurement apparatus according to claim 1 and comprising:
   a heat sink for stabilizing the temperature of the detector;
   and wherein said chopper is operative to alternatively reflect to the detector radiation from the detector and direct to the detector radiation received from the object; and
   calculation means for providing an output indication representing the temperature of the object in response to the output of the detector.

5. Temperature measurement apparatus according to claim 4 and also comprising means for analyzing and indicating menstrual status by employing said output indication.

6. Temperature measurement apparatus according to claim 1 and also comprising means for analyzing and indicating menstrual status by employing said output indication.

7. Temperature measurement apparatus according to claim 1 and also comprising:
   a memory storing a multiplicity of temperatures of said object taken over a period of time; and
   means for analyzing said multiplicity of temperatures and for indicting, as a result of the analysis, menstual status.

8. Apparatus according to claim 1 and wherein said means for providing an output indication comprises a microprocessor which is also operative to directly drive the quartz timepiece movement assembly to drive the chopper blade in reciprocating rotational movement.

9. Apparatus according to claim 1 and also comprising mechanical limiting means for physically limiting the rotation of said chopper blade to a predetermined azimuth.

* * * * *